United States Patent [19]

Gehrer et al.

[11] Patent Number: 5,298,668

[45] Date of Patent: Mar. 29, 1994

[54] CATALYTIC PREPARATION OF FORMALDEHYDE CONDENSATES

[75] Inventors: Eugen Gehrer, Ludwigshafen; Wolfgang Harder, Weinheim; Klaus Ebel, Ludwigshafen; Johann-Peter Melder, Mannheim; Joaquim H. Teles, Ludwigshafen, all of Fed. Rep. of Germany

[73] Assignee: BASF Aktiengesellschaft, Ludwigshafen, Fed. Rep. of Germany

[21] Appl. No.: 37,884

[22] Filed: Mar. 26, 1993

[51] Int. Cl.$^5$ .............................................. C07C 45/72
[52] U.S. Cl. ................................. 568/463; 568/458
[58] Field of Search .................... 568/458, 463, 464

[56] References Cited

U.S. PATENT DOCUMENTS

| | | | |
|---|---|---|---|
| 2,224,910 | 12/1940 | Hanford et al. | 568/463 |
| 3,865,850 | 2/1975 | Merger | 568/464 |
| 4,615,970 | 10/1986 | Kojima et al. | 430/446 |
| 5,144,088 | 9/1992 | Salek et al. | 568/458 |

FOREIGN PATENT DOCUMENTS

| | | | |
|---|---|---|---|
| 0262029 | 11/1988 | Fed. Rep. of Germany | 568/463 |
| 1608182 | 11/1990 | U.S.S.R. | 568/463 |

OTHER PUBLICATIONS

Tetrahedron Letters, vol. pp. 4517–4520 (1980).

*Primary Examiner*—Werren B. Lone
*Attorney, Agent, or Firm*—John H. Shurtleff

[57] ABSTRACT

Arycolaldehyde, glyceraldehyde, C$_4$- and C$_5$-sugars or mixtures thereof are prepared in a self-condensation of formaldehyde by reacting formaldehyde or a formaldehyde donor in the presence of a mesoionic catalyst of the formula

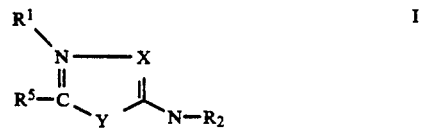

I wherein X is nitrogen or CR$^3$, Y is sulfur or selenium or NR$^4$, and R$^1$, R$^2$, R$^3$ and R$^4$ can be identical or different and each can represent an aliphatic, aryl, aralkyl or heteroaryl group which is unsubstituted or which bears substituents which have only a negligible effect on the catalytic activity of said mesoionic catalyst, with the proviso that R$^2$ together with R$^4$ can form a C$_2$–C$_5$-alkylene or alkenylene bridge or a C$_6$–C$_{14}$-arylene bridge, and wherein R$^5$ is hydrogen, the hydroxymethyl group -CH$_2$OH or the hydroxymethylhydroxymethyl group —CH(OH)(CH$_2$OH).

14 Claims, No Drawings

CATALYTIC PREPARATION OF FORMALDEHYDE CONDENSATES

The invention relates to a process for the catalytic preparation of formaldehyde condensates.

It has been known since the work of J. Castells (Tetrahedron Letters, 21 (1980) 4517–4520) that thiazolium ylides can be used as catalysts for the catalytic umpolung of formaldehyde and thus for its self-condensation to give dihydroxyacetone, and likewise for the corresponding conversion of higher aldehydes into acyloins.

Acyloin condensation of formaldehyde with thiazolium ylides as catalysts results mainly in ketones, especially dihydroxyacetone (DHA). It is an object of the present invention to find a process and novel catalysts for the condensation of formaldehyde which provide in this reaction a spectrum of products differing from that with thiazolium ylides and which, in particular, make it possible to prepare glycolaldehyde and/or glyceraldehyde with good selectivity. It is, in particular, impossible to obtain glycolaldehyde using thiazolium ylide catalysts. Glycolaldehyde and glyceraldehyde are valuable intermediates for the preparation of ethylene glycol, glyoxal, glycerol and for synthesizing active substances.

We have found that this object is achieved by a process for the catalytic preparation of formaldehyde condensates, which comprises reacting formaldehyde or formaldehyde donors in the presence of mesoionic catalysts of the formula I

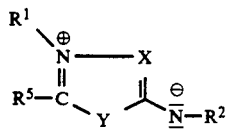

where

X is nitrogen or $CR^3$,

Y is sulfur or selenium or $NR^4$, and where $R^1$, $R^2$ and $R^3$ are identical or different and are each aliphatic groups with 1–30 carbons, unsubstituted or substituted aryl groups, unsubstituted or substituted aralkyl groups and/or unsubstituted or substituted heteroaryl groups, $R^4$ is an aliphatic group with 1–30 carbons, unsubstituted or substituted aryl, unsubstituted or substituted aralkyl or unsubstituted or substituted heteroaryl, or where $R^2$ forms together with $R^4$ a $C_2$–$C_5$-alkylene or alkenylene or a $C_6$–$C_{14}$-arylene bridge, and where $R^5$ is hydrogen, hydroxymethyl -$CH_2OH$ or hydroxymethylhydroxymethyl —$CH(OH)(CH_2OH)$.

The catalysts used according to the invention thus comprise mesoionic compounds which are dipolar, five-membered heterocycles which have a center of positive charge and a center of negative charge in the same molecule so that they are overall neutral although it is not possible to depict a limiting mesomeric structure in which the positive and negative charges are not present.

The purpose of $R^1$, $R^2$, $R^3$ and $R^4$ is essentially to stabilize the mesoionic catalysts, ie. to ensure by their presence that the dipolar molecules cannot rearrange to give other non-mesoionic molecules which do not have separate centers of positive and negative charge. These radicals may therefore have a large number of meanings.

Thus, $R^1$, $R^2$ and $R^3$ can be identical or different and be aliphatic groups with 1–30 carbons such as $C_1$–$C_{30}$-alkyl, preferably $C_1$–$C_{10}$-alkyl, $C_2$–$C_{30}$, preferably $C_2$–$C_{10}$-alkenyl or alkynyl with 1 or 2, preferably only one, multiple bond, $C_3$–$C_{20}$, preferably $C_1$–$C_{10}$-cycloalkyl or -alkenyl, $C_3$–$C_{20}$-heterocycloalkyl or -alkenyl, such as piperidinyl, piperazinyl, pyrrolidinyl, imidazolidinyl, tetrahydrothienyl, tetrahydrofuranyl, tetrahydropyranyl, thiazolidinyl, oxazolidinyl, imidazolinyl, thiazolinyl, oxazolinyl or crown ether groups, $C_2$–$C_{30}$-preferably $C_2$–$C_{10}$-oxaalkyl which has one or more, preferably only one, oxygen in the ether chain and is bonded via a carbon atom to the basic framework of the catalyst I, $C_1$–$C_{30}$-, preferably $C_1$–$C_{10}$-haloalkyl which contains one or more, preferably 1 to 3, fluorine, chlorine and/or bromine, preferably fluorine and/or chlorine, in particular fluorine, atoms, and in the case of fluoroalkyl advantageously perfluoroalkyl, or aminoalkyl such as $C_2$–$C_{30}$-, preferably $C_2$–$C_{20}$-alkylaminoalkyl or $C_3$–$C_{30}$-, preferably $C_3$–$C_{21}$-dialkylaminoalkyl, or unsubstituted or substituted aryl, preferably $C_6$–$C_{14}$-aryl, in particular phenyl, naphthyl, anthryl or phenanthryl, unsubstituted or substituted $C_7$–$C_{20}$-aralkyl, especially benzyl, phenylethyl or naphthylmethyl, unsubstituted or substituted $C_2$–$C_{15}$-heteroaryl with 1 to 3 nitrogens or one oxygen or sulfur or with 1 to 2 nitrogens and one oxygen or sulfur in the ring, such as furanyl, thienyl, pyrrolyl, pyrazolyl, imidazolyl, thiazolyl, isothiazolyl, oxazolyl, isoxazolyl, pyridinyl, pyrimidinyl, pyrazinyl, quinolinyl, naphthyridinyl, 1,2,4-triazolyl or acridinyl.

Both the aliphatic and aromatic and, of course, also the aralkyl radicals can be substituted one or more times, preferably not more than three times, by halogen, nitro, hydroxyl, cyano, alkyl, alkoxy or unsubstituted, mono- or disubstituted amino. Since these substituents have, as a rule, only a slight effect on the catalytic activity of the relevant catalysts I, preferably used, mainly because of their low-cost preparation, are the above-mentioned unsubstituted $R^1$, $R^2$ and $R^3$ radicals.

$R^4$ can be identical to or different from $R^1$, $R^2$ and $R^3$ and can also, together with $R^2$, form a $C_2$–$C_5$-alkylene or alkenylene bridge or a $C_6$–$C_{14}$-arylene bridge, preferably an o-phenylene, o-naphthylene, 1,8-naphthylene, o-fluorenylene, 4,5-fluorenylene, o-phenanthrylene, 4,5-phenanthrylene, 9,10-phenanthrylene, 2,2'-biphenylene, o-anthrylene or 1,9-anthrylene bridge.

Particularly preferred catalysts of the formula Ia

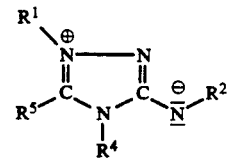

where $R^1$, $R^2$, $R^4$ and $R^5$ have the abovementioned meanings. Preferred catalysts of the formula Ia in turn are those where $R^1$, $R^2$ and $R^4$ are each unsubstituted or substituted aryl, especially unsubstituted or substituted phenyl, and $R^5$ has the abovementioned meanings. Particularly preferably used in the process according to the invention is nitron (1,4-diphenyl-3-(phenylamino)-1H-1,2,4-triazolium hydroxide, inner salt) of the formula Ib.

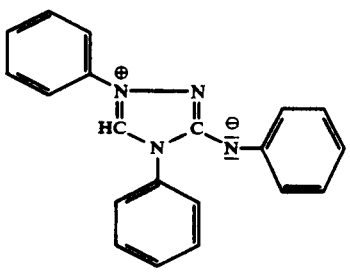

The formaldehyde in the process according to the invention can be in the form of formaldehyde or of formaldehyde donors, eg. paraformaldehyde, formaldehyde hemiacetal solutions, gaseous formaldehyde or aqueous solution (Formalin ®). It is generally stirred together with an organic solvent and the catalyst at 20°–160° C., preferably 50°–120° C., and particularly preferably 60°–80° C. for, expediently, 5–500 minutes, preferably 15–60 minutes.

The pressure is generally not critical for the process according to the invention. It is therefore expediently carried out under atmospheric pressure or under the autogenous pressure of the reaction system.

As a rule, no base is necessary for carrying out the reaction. However, since small amounts of acids may be formed as byproducts in the reaction, eg. formic acid by Cannizzaro reaction, and these acids may inactivate the catalyst, it may be advantageous to add a base such as triethylamine, alkali metal or alkaline earth metal carbonate, alkali metal or alkaline earth metal hydroxide, buffers such as phosphate buffer, acetate buffer etc. to buffer these acids. This may be particularly beneficial when very small amounts of catalyst are used.

The use of a base is accordingly also expedient when the catalyst is used in the form of its catalytically less active adducts with carboxylic acids or mineral acids, ie. as onium salt, in the process according to the invention. In this case, the acid bound to the catalyst can be neutralized by adding a non-nucleophilic base, eg. formates or acetates or a tri-$C_1$–$C_8$, preferably $C_1$–$C_4$-alkylamine, or pyridines, to activate the catalyst.

The process according to the invention is expediently carried out in the presence of a solvent. Suitable solvents belong in principle to a very wide spectrum, such as alcohols, eg. methanol, ethanol, propanol, cyclohexanol, 2-ethylhexanol and hexadecyl alcohol, amides, eg. dimethylformamide (DMF), dibutylformamide, ureas such as dimethylethyleneurea, dimethylpropyleneurea, carbonates, eg. propylene carbonate, ethylene carbonate, aromatic solvents, eg. toluene, heterocycles, eg. pyridine, N-methylimidazole, N-methylpyrrolidone, ketones, eg. acetone, esters, eg. ethyl acetate, ethers, eg. methyl tert-butyl ether, diethylene glycol methyl ether, tetrahydrofuran, aromatic nitro compounds, eg. nitrotoluene, tertiary amines, eg. triethylamine, halohydrocarbons such as chlorobenzene or dichlorobenzene, sulfides such as dimethyl sulfoxide, sulfones such as dimethyl sulfone or sulfolane (tetrahydrothiophene 1,1-dioxide), trioxane and nitriles, eg. acetonitrile or propionitrile. The amount of solvent is not generally critical and depends on the nature of the solvent, which is why it is expedient to determine in a preliminary test the optimal amount of the solvent to be used in each case.

The molar ratio of formaldehyde to catalyst can be in the range from 10:1 to 10000 1. When the formaldehyde/catalyst molar ratio is more than 200 it may be advantageous to add a base or a buffer to trap the acids.

The use of the catalysts of the formula I is, according to the invention, equated to the use of their synthetic precursors. Thus, it is possible to use these precursors in place of these catalysts in the process according to the invention, because the mesoionic catalysts I are formed in situ from these precursors in the reaction mixture under the conditions normally used in the process according to the invention. For example, the reaction of triphenylaminoguanidine of the formula III with formaldehyde according to Equation (1)

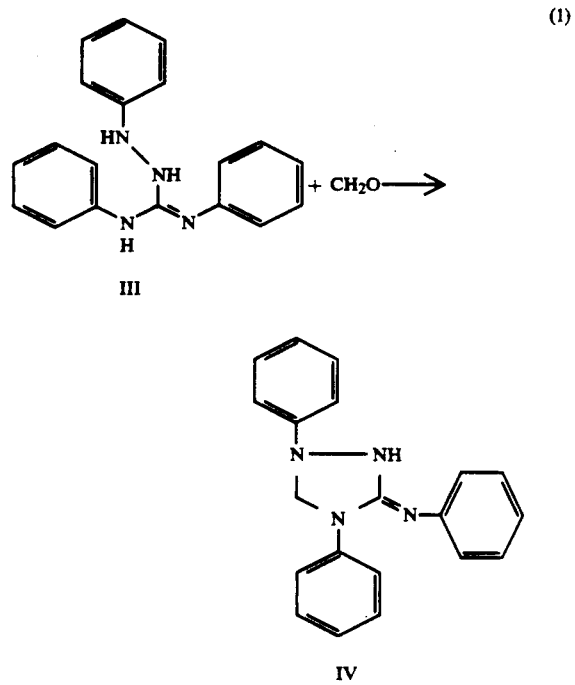

under the conditions used in the process according to the invention leads to the formation of dihydronitron of the formula IV, which in turn is easily oxidized by oxidizing agents, eg. atmospheric oxygen, into nitron of the formula Ib, which is the actual catalytically active compound. The same effect is achieved by reacting the guanidine III with formic acid in the reaction mixture. In this case there is immediate formation of nitron Ib without passing through the stage of the intermediate IV. These two procedures can also be used for in situ generation of the other mesoionic compounds which can be used according to the invention, especially those of the formula Ia, from the corresponding substituted amino-guanidine compounds of the formula II

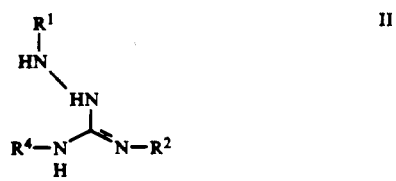

where $R^1$, $R^2$ and $R^4$ have the abovementioned meanings. When formic acid is added to the mixture of aminoguanidine II and formaldehyde for in situ generation of the catalytically active compounds I, it is unnecessary, as explained above, for an oxidizing agent to be present.

The reaction can be carried out either in homogeneous phase or in suspension or else in a liquid two-phase system. In the latter case, aqueous formaldehyde is employed as raw material, for example, and the catalyst is dissolved in an organic, water-immiscible solvent, preferably a long-chain, in particular $C_6$-$C_{20}$-alcohol. Under these phase-transfer conditions, the formaldehyde is extracted into the organic phase and reacts on the catalyst therein, and the hydrophilic product (glycolaldehyde, glyceraldehyde) is back-extracted into the aqueous phase.

The process according to the invention can be used to prepare formaldehyde condensates, especially glycolaldehyde, glyceraldehyde and $C_4$ sugars, the choice of the catalyst I allowing control. The mechanism forming the basis for this reaction has not yet been completely elucidated. It is, however, assumed that the catalytically active center is located on position 5 of the mesoionic catalysts I according to the invention. The reason for this assumption is that on reaction of catalysts I with formaldehyde it is possible to isolate catalyst-formaldehyde adducts in which $R^5$ is —$CH_2OH$ or —CH(OH)($CH_2OH$), which themselves have catalytic activity. It is very surprising that, using the catalysts according to the invention, there is principally formation of the abovementioned formaldehyde condensates, whereas dihydroxyacetone is produced in only small quantities. This catalytic behavior is in clear contrast to the behavior of thiazolium ylide catalysts which provide mainly dihydroxyacetone, but no glycolaldehyde, on condensation of formaldehyde.

Nitron is commercially available or can be prepared by reacting triphenylaminoguanidine with formic acid as described by Busch and Mehrtens, Ber. 38 (1905) 4049. The other nitron derivatives which can be used according to the invention can also be generated similarly from appropriately substituted aminoguanidines and formic acid.

EXAMPLES

Examples 1

A mixture of 4.0 g (133 mmol) of paraformaldehyde, X g (see table) of nitron, 15.8 g of ethyl acetate and 0.2 g of molecular sieves was stirred in a glass pressure vessel at 80° C. for 15 minutes. The results of the reactions were as follows:

| Amount of nitron [g] | Formaldehyde/ molar ratio | Conversion [%] | Selectivity in % | |
|---|---|---|---|---|
| | | | Glycolaldehyde | Glyceraldehyde |
| 0.201 | 207 | 29.4 | 86.2 | 10.1 |
| 0.103 | 405 | 19.2 | 90.1 | 7.0 |
| 0.051 | 816 | 12.6 | 91.0 | 5.4 |
| 0.025 | 1695 | 6.2 | 94.3 | 2.8 |

Examples 2

A mixture of 3.9 g (130 mmol) of paraformaldehyde, 0.26 g (0.87 mmol) of nitron, 15.8 g of ethyl acetate and 0.2 g of molecular sieves was stirred in a glass pressure vessel at 80° C. for 60 minutes. Samples were taken and analysed after 15, 30 and 60 minutes.

| Yields in % based on formaldehyde | | | |
|---|---|---|---|
| Reaction time | Glycolaldehyde | Glyceraldehyde | Dihydroxyacetone |
| 15 min | 36.0% | 15.2% | 0.3% |
| 30 min | 44.8% | 24.9% | 0.5% |
| 60 min | 45.8% | 35.0% | 1.1% |

Example 3

A two-phase mixture of 4.83 g (60 mmol) of Formalin ® (37% strength), 5 g of chloroform and 0.47 g (1.52 mmol) of nitron was vigorously stirred in a glass pressure vessel at 80° C. for 60 minutes. Samples were taken and analyzed after 15, 30 and 60 minutes. Yields in % based on formaldehyde

| Reaction time | Glycolaldehyde | Glyceraldehyde |
|---|---|---|
| 15 min | 23.9% | 15.3% |
| 30 min | 23.8% | 15.7% |
| 60 min | 23.0% | 14.0% |

Example 4

This example demonstrates that a broad spectrum of solvents is suitable, and moderately polar solvents (chloroform, tetrahydrofuran, pyridine) are particularly preferred for high glycolaldehyde selectivity.

A mixture of 2 g (66.7 mmol) of paraformaldehyde, 0.1 g (0.33 mmol) of nitron, 7.9 g of solvent and 0.1 g of molecular sieves was stirred at 80° C. for 30 minutes.

| | Yields in % based on formaldehyde | | |
|---|---|---|---|
| Solvent | Glycolaldehyde | Glyceraldehyde | Higher sugars (C4 + C5) |
| Methanol | 5.6 | 6.8 | 16.9 |
| Ethanol | 12.7 | 7.5 | 3.3 |
| n-Propanol | 15.4 | 11.0 | 5.1 |
| i-Propanol | 21.8 | 14.0 | 4.9 |
| t-butanol | 36.9 | 12.9 | 2.7 |
| Cyclohexanol | 20.8 | 12.4 | 4.5 |
| 2-Ethylhexanol | 24.1 | 20.9 | 9.5 |
| Hexadecanol | 8.6 | 5.4 | 3.8 |
| DMF | 23.5 | 4.6 | 0.4 |
| Dibutylformamide | 0.6 | 0.1 | 4.5 |
| Dimethylethylene carbonate | 8.4 | 1.9 | 7.4 |
| Toluene | 6.1 | 6.5 | 6.7 |
| Pyridine | 46.4 | 8.2 | 1.7 |
| N-Methylimidazole | 18.1 | 10.7 | 4.7 |
| N-Methylpyrrolidone | 7.0 | 0.6 | 0.7 |
| Water | 0.6 | 0.6 | 0.8 |
| Acetone | 32.0 | 5.5 | 0.5 |
| Ethyl acetate | 59.4 | 10.9 | 2.2 |
| Methyl tert-butyl ether | 0.3 | 0.3 | 0.0 |
| Diethylene glycol dimethyl ether | 41.6 | 5.0 | 0.2 |
| Tetrahydrofuran | 56.6 | 14.1 | 3.4 |
| Nitrotoluene | 15.8 | 4.5 | 0.8 |
| Nitroethane | 0.8 | 0.4 | 0.2 |
| Acetonitrile | 15.8 | 2.9 | 0.2 |
| Chloroform | 53.3 | 21.4 | 7.7 |
| Propylene glycol | 4.9 | 9.5 | 18.6 |
| Triethylamine | 1.9 | 3.7 | 17.6 |
| Trioxane | 27.4 | 6.4 | 1.6 |

Example 5

This example shows that the reaction can be carried out in a wide temperature range.

In each case a suspension of 20% by weight paraformaldehyde in DMF was stirred with the catalyst nitron at the stated temperature for the stated time.

| Temperature | Catalyst/formaldehyde*) | Time | Yields in % based on fromaldehyde. | | |
|---|---|---|---|---|---|
| | | | Glycolaldehyde | Glyceraldehyde | DHA |
| 20° C. | 1:100 | 1 h | 1.3% | — | — |
| 20° C. | 1:100 | 4 h | 3.8% | — | — |
| 20° C. | 1:100 | 24 h | 10.9% | 0.2% | 0.7% |
| 40° C. | 1:100 | 1 h | 5.7% | 0.4% | — |
| 40° C. | 1:100 | 4 h | 14.2% | 1.2% | 0.1% |
| 40° C. | 1:100 | 24 h | 17.1% | 3.4% | 0.5% |
| 60° C. | 1:100 | 0.5 h | 15.5% | 1.4% | 0.1% |
| 60° C. | 1:100 | 1 h | 20.0% | 2.4% | 0.2% |
| 60° C. | 1:100 | 2 h | 22.0% | 4.0% | 0.3% |
| 80° C. | 1:200 | 0.5 h | 17.2% | 2.3% | 0.3% |
| 80° C. | 1:200 | 1 h | 18.4% | 4.3% | 0.5% |
| 80° C. | 1:200 | 2 h | 20.7% | 7.6% | 0.7% |
| 100° C. | 1:400 | 15 min | 21.5% | 4.1% | 0.3% |
| 100° C. | 1:400 | 30 min | 23.3% | 8.1% | 0.5% |
| 100° C. | 1:400 | 60 min | 22.0% | 13.7% | 0.7% |
| 120° C. | 1:1000 | 15 min | 19.4% | 11.5% | 0.5% |
| 120° C. | 1:1000 | 30 min | 13.4% | 19.2% | 0.8% |
| 140° C. | 1:1000 | 15 min | 7.5% | 19.0% | 5.2% |
| 140° C. | 1:1000 | 30 min | 1.6% | 0.8% | 10.1% |

*)molar ratio
All the reaction mixtures were analyzed by gas chromatography.

Preparation of the Catalysts

Triphenylaminoguanidine II 100 g (0.44 mol) of N,N'-diphenylthiourea were suspended in 300 ml of toluene and stirred with 100 g (0.45 mol) of PbO at 80° C. for 15 minutes (until all the black PbS has precipitated). The hot solution was filtered, and 50 g (0.46 mol) of phenylhydrazine were added to the filtrate. This solution was stirred at 80° C. for 30 minutes. The product crystallized out on cooling.

1,4-di-(2-Methylphenyl)-3-(2-methylphenylamino)-1H-1,2,4-triazolium hydroxide, inner salt VI 1.4 g (3.67 mmol) of tri-(2-methylphenyl)aminoguanidine (prepared as described by Busch, Ber. 38 (1905) 856 by reacting 2-methylphenylhydrazine with di-(2-methylphenyl)carbodiimide (prepared as described by Campbell et al.: J. Am. Chem. Soc. 84 (1962) 3673 were stirred with 7 ml of concentrated formic acid in a glass pressure vessel at 140° C. for 20 hours. After cooling, the reaction mixture was diluted with water, neutralized with ammonia and extracted with chloroform. The organic phase was dried over sodium sulfate, the solvent was removed by distillation, and the residue was chromatographed on silica gel first with diethyl ether and then with methanol as eluent.

Melting point: 160°-165° C.
Mass spectrum: molecular peak: 354 m/e.

A similar reaction of phenylhydrazine with di-(2-methylphenyl)carbodiimide and subsequent cyclization of the resulting condensate with formic acid resulted in 1-phenyl-4-(2-methylphenyl)-3-(2-methylphenylamino)-1H-1,2,4-triazolium hydroxide, inner salt V.

Naphthonitron hydroiodide
(9-phenyl-7H-1,2,4-triazolo-4,3-a]perimidinium iodide) VII 28.1 ml (286 mmol) of phenylhydrazine were added to a suspension of 19.2 g (56 mmol) of 2-(methylthio)-perimidinium iodide, which had been prepared as described by Herbert et al., J. Med. Chem. 30 (1987) 2081, in 120 ml of methanol, and the resulting mixture was refluxed for 2 h. After the reaction was complete, the solvent was removed and the resinous residue was digested with 30 ml of methanol for 2 h. The resulting precipitate was filtered off, washed with a little cold methanol and dried in a desiccator. The results of the NMR spectroscopy and mass spectrometry, and of the elemental analysis showed that the resulting solid was 2-(N'-phenylhydrazino)perimidinium iodide. 2.0 g (5.0 mmol) of this compound were stirred with 10 ml of concentrated formic acid in a 25 ml glass autoclave at 175° C. for 2 hours. After cooling, the solution was mixed with 130 ml of water, and the precipitated solid was filtered off and recrystallized from ethanol.

Mass spectrum: molecular peak 285 m/e
Melting point: >300° C.
Elemental analysis correct, 1-Phenyl-3-cyclohexylamino-4-cyclohexyl-1H-1,2,4-tria-zolium formate VIII 10.6 g (98 mmol) of phenylhydrazine were added to 20.0 g (98 mmol) of N,N'-dicyclohexylcarbodiimide (obtainable by the process of J. Am. Chem. Soc. 84 (1962) 3673 from cyclohexyl isocyanate) in 900 ml of toluene at 40° C. The mixture was then stirred at room temperature for 2 h and subsequently the solvent was removed by distillation under reduced pressure. The residue was mixed with 4.5 g of formic acid and 100 ml of diethyl ether, whereupon a solid precipitated. After removal of the ether, 54.8 g of formic acid were added to the solid, and the mixture was heated at 112° C. for 20 h. The mixture was cooled to room temperature, mixed with 500 ml of water, insolubles were removed by filtration, and the resulting solution was made weakly basic with aqueous ammonia. The resulting precipitate was filtered off and dissolved in dichloromethane. The solid remaining after drying over sodium sulfate and removal of the solvent was recrystallized from ethanol.

Mass spectrum: molecular peak 325 m/e
Melting point: 178° C.

Standard test for catalytic activity

The mesoionic compounds described above were investigated for their catalytic activity in the process according to the invention as follows. 2.0 g (66.7 mmol) of paraformaldehyde were suspended in 18 g of dimethylformamide. To this suspension was added 0.33 mmol of the mesoionic catalyst (formaldehyde/catalyst molar ratio =200:1) and this mixture was stirred at 80° C. for 1 h. If the catalysts were employed in the form of their onium salts (catalysts VII and VIII), the active catalyst was liberated therefrom by adding 1 equivalent of triethylamine.

The reaction products were analyzed as follows: 0.5 g of reaction product was mixed with 10 g of oximation reagent (5.0 g of 1,4-butanediol as internal standard for the gas chromatography and 70 g of hydroxylamine hydrochloride in 1000 g of pyridine) and heated at 70° C. for one hour. 1 ml of this solution was then mixed with 1 ml of hexamethyldisilazane and 1 ml of trimethylsilyl chloride and left to stand at room temperature for 0.5–1 h until pyridinium chloride precipitated in large flakes. The mixture was filtered, and the resulting solution was used directly for determination of the products by gas chromatography.

The results obtained with the individual catalysts are listed in the following table. The meanings of the abbreviations in this table are: GA—glycolaldehyde; GlyAld—glyceraldehyde; DHA—dihydroxyacetone; C₄—mixture of C₄ carbohydrates (tetroses); Et₃N—triethylamine.

TABLE
Standard tests with the catalysts Ib, V, VI, VII and VIII and with catalyst precursor III

| Catalyst | Time min | Temp. [°C.] | Base | GA | GlyAld | DHA | C₄ |
|---|---|---|---|---|---|---|---|
| Ib | 60 | 80 | — | 65.2 | 16.0 | 0.8 | 1.2 |
| V | 60 | 80 | — | 50.7 | 21.7 | 0.4 | 1.3 |
|   | 60 | 100 | — | 55.4 | 34.4 | 0.6 | 2.7 |
| VI | 60 | 80 | — | 31.5 | 26.2 | 3.3 | 5.7 |
| VII | 60 | 80 | Et₃N | 3.5 | — | — | — |
|   | 60 | 100 | Et₃N | 7.6 | 1.1 | — | — |
| VIII | 60 | 80 | — | 13.5 | 18.9 | 0.3 | 3.3 |
|   | 60 | 80 | Et₃N | 10.6 | 19.5 | 0.7 | 4.5 |

TABLE-continued

Standard tests with the catalysts Ib, V, VI, VII and VIII and with catalyst precursor III

| Catalyst | Time min | Temp. [°C.] | Base | GA | GlyAld | DHA | C₄ |
|---|---|---|---|---|---|---|---|
| | 60 | 80 | — | 18.9 | 3.6 | — | — |
| | 60 | 100 | — | 45.2 | 42.4 | 0.7 | 6.2 |

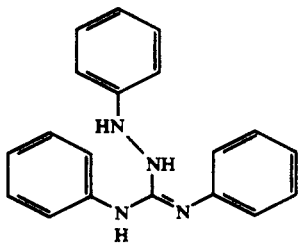

III

We claim:

1. A process for the preparation of glycolaldehyde, glyceraldehyde, C₄-and C₅-sugars or mixtures thereof by self-condensation of formaldehyde which comprises: reacting formaldehyde or a formaldehyde donor in the presence of a mesoionic catalyst of the formula

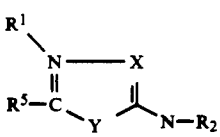

I wherein X is nitrogen or $CR^3$, Y is sulfur or selenium or $NR^4$, and $R^1$, $R^2$, $R^3$ and $R^4$ can be identical or different and each can represent an aliphatic, aryl, aralkyl or heteroaryl group which is unsubstituted or which bears substituents which have only a negligible effect on the catalytic activity of said mesoionic catalyst, with the proviso that $R^2$ together with $R^4$ can form a $C_2$-$C_5$-alkylene or alkenylene bridge or a $C_6$-$C_{14}$-arylene bridge, and wherein $R^5$ is hydrogen, the hydroxymethyl group —CH₂OH or the hydroxymethylhydroxymethyl group —CH(OH)(CH₂OH).

2. A process as claimed in claim 1, wherein the formaldehyde or formaldehyde donors are reacted in the presence of mesoionic catalysts of the formula I

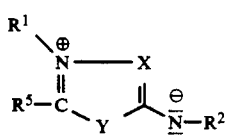

I where
X is nitrogen or $CR^3$,
Y is sulfur or selenium or $NR^4$, and where
$R^1$, $R^2$ and $R^3$ are identical or different and are each $C_1$-$C_{30}$-alkyl, $C_2$-$C_{30}$-alkenyl or alkynyl with 1 or 2 multiple bonds, $C_3$-$C_{20}$-cycloalkyl or -alkenyl, $C_3$-$C_{20}$-hetero-cycloalkyl or -alkenyl, or $C_2$-$C_{30}$-oxaalkyl which has one or more oxygen atoms in the ether chain and is bonded via a carbon atom to the basic framework of catalyst I, or $C_1$-$C_{30}$-haloalkyl which contains one or more fluorine, chlorine or bromine atoms, or $C_2$-$C_{30}$-alkylaminoalkyl or $C_3$-$C_{30}$-dialkylaminoalkyl, or unsubstituted or substituted $C_6$-$C_{14}$-aryl, unsubstituted or substituted $C_7$-$C_{20}$-aralkyl, and/or unsubstituted or substituted $C_2$-$C_{15}$-hetero-aryl with 1 to 3 nitrogens or one oxygen or sulfur or with 1 to 2 nitrogens and one oxygen or sulfur in the ring, $R^4$ is identical to or different from $R^1$, $R^2$ or $R^3$ or forms together with $R^2$ a $C_2$-$C_5$-alkylene or alkenylene or a $C_6$-$C_{14}$-arylene bridge, and where $R^5$ is hydrogen, hydroxymethyl -CH₂OH or hydroxymeth-ylenehydroxymethyl -CH(OH)(CH₂OH).

3. A process as claimed in claim 1, wherein the catalyst is a mesoionic triazolium compound of the formula Ia

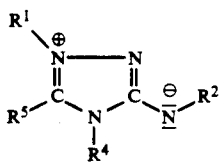

Ia where $R^1$, $R^2$, $R^5$ and $R^4$ have the meanings specified in claim 1.

4. A process as claimed in claim 1, wherein the catalyst is nitron of the formula Ib

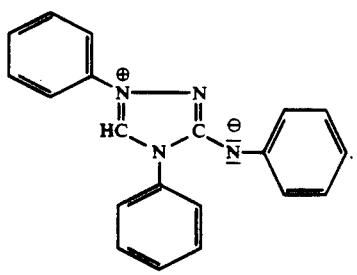

Ib

5. A process as claimed in claim 1, wherein the catalyst of the formula Ia is generated in situ in the reaction mixture from aminoguanidine compounds of the formula II

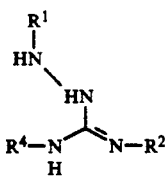

where $R^1$, $R^2$ and $R^4$ have the meanings specified in claim 1, and formic acid, or from the aminoguanidine compounds II and formaldehyde in the presence of an oxidizing agent.

6. A process as claimed in claim 1, wherein the mesoionic catalyst I is employed in the form of its onium salt with a carboxylic acid or mineral acid, and the catalyst I is liberated therefrom with the aid of a base.

7. A process as claimed in claim 1, wherein the mesoionic catalys is 1,4-di-(2-methylphenyl)-3-(2-methyl-phenyl-amino) -1H-1,2,4-triazolium hydroxide, inner salt.

8. A process as claimed in claim 1, wherein the mesoionic catalyst is 1-phenyl-4-(2-methylphenyl)-3-(2-methyl-phenylamino) -1H-1,2,4-triazolium hydroxide, inner salt.

9. A process as claimed in claim 1, wherein the mesoionic catalyst is naphthonitron hydroiodide.

10. A process as claimed in claim 1, wherein the mesoionic catalyst is 1-phenyl-3-cyclohexylamino-4-cyclohexyl-1H-1,2,4-triazolium formate.

11. A process as claimed in claim 1, wherein the reaction is carried out at a temperature of from 20° to 160° C.

12. A process as claimed in claim 1, wherein the reaction is carried out under atmospheric pressure or the autogenous pressure of the reaction system.

13. A process as claimed in claim 1, wherein the reaction is carried out using a molar ratio of formaldehye to catalyst of from 10:1 to 10,000:1.

14. A process as claimed in claim 13, wherein said molar ratio is more than 200:1, and a base or buffer is added to the reaction mixture to trap acids.

* * * * *

UNITED STATES PATENT AND TRADEMARK OFFICE
CERTIFICATE OF CORRECTION

PATENT NO. : 5,298,668
DATED : March 29, 1994
INVENTOR(S) : Gehrer et al.

It is certified that error appears in the above-identified patent and that said Letters Patent is hereby corrected as shown below:

On title page, item [57] Abstract

In the first line of the Abstract change "arycolaaldehyde" to ---Glycolaldehyde---.

IN THE CLAIMS:

Col. 12, claim 2, line 27, change "and/or" to --or--

Col. 13, claim 7, line 20, change "catalys" to --catalyst--.

Signed and Sealed this

Eighth Day of November, 1994

Attest:

BRUCE LEHMAN

Attesting Officer     Commissioner of Patents and Trademarks